US006542578B2

(12) United States Patent  
Ries et al.

(10) Patent No.: US 6,542,578 B2
(45) Date of Patent: Apr. 1, 2003

(54) APPARATUS FOR DETERMINING THE CRYSTALLINE AND POLYCRYSTALLINE MATERIALS OF AN ITEM

(75) Inventors: Hermann Ries, Taunusstein (DE); Patricia Schall, Darmstadt (DE); Frank Cordes, Neustadt (DE); Martin Hartick, Bad Nauheim (DE)

(73) Assignee: Heimann Systems GmbH, Wiesbaden (DE)

( * ) Notice: Subject to any disclaimer, the term of this patent is extended or adjusted under 35 U.S.C. 154(b) by 0 days.

(21) Appl. No.: 10/080,762

(22) Filed: May 16, 2001

(65) Prior Publication Data

US 2002/0181656 A1 Dec. 5, 2002

Related U.S. Application Data

(63) Continuation of application No. 09/645,486, filed on Aug. 25, 2000, now abandoned.

(30) Foreign Application Priority Data

Nov. 13, 1999 (DE) .......................................... 199 54 664

(51) Int. Cl.⁷ .................................................. G21K 1/02
(52) U.S. Cl. .................................. 378/147; 250/370.09
(58) Field of Search .............................. 378/57, 58, 73, 378/88, 90, 146, 147, 145; 250/370.08, 370.09, 370.1

(56) References Cited

U.S. PATENT DOCUMENTS

| 4,956,856 | A |   | 9/1990  | Harding ........................ 378/88  |
| 4,986,273 | A | * | 1/1991  | O'Neill et al. ............... 600/425 |
| 5,008,911 | A | * | 4/1991  | Harding ........................ 378/86  |
| 5,265,144 | A |   | 11/1993 | Harding et al. ............... 378/86  |
| 5,491,738 | A | * | 2/1996  | Blake et al. .................. 378/71  |
| 5,787,145 | A |   | 7/1998  | Geus ............................. 378/71 |
| 6,005,913 | A | * | 12/1999 | Zombo et al. ................. 378/71  |
| 6,282,264 | B1 | * | 8/2001 | Smith et al. ................. 378/189 |
| 6,393,085 | B1 | * | 5/2002 | Heller et al. ................ 376/158 |

FOREIGN PATENT DOCUMENTS

| DE | 39 09 147 A1 | 4/1991 |
| DE | 41 30 039 A1 | 3/1993 |
| DE | 41 01 544 A1 | 11/1993 |
| DE | 195 10 168 A1 | 7/1998 |
| DE | 197 45 669 A1 | 5/2002 |
| EP | 0 354 045 | 2/1990 |
| WO | WO 99/66317 A1 | 12/1999 |

OTHER PUBLICATIONS

H. Strecker, "Automatic detection of explosives in airline baggage using electic X–ray scatter", MedicMundi, 1998, 42 (2), pp. 30–33.

Helmut Strecker, "Atomatishe Gepackkontrolle mit Rontgenstreustrahlung", Technische Physik, 1999.

(List continued on next page.)

Primary Examiner—Drew A. Dunn
Assistant Examiner—Courtney Thomas
(74) Attorney, Agent, or Firm—Birch, Stewart, Kolasch & Birch, LLP

(57) ABSTRACT

A diffraction apparatus (10) for determining crystalline and polycrystalline materials of an item in objects, preferably in luggage, having a collimation/detector arrangement (11) and an X-ray source (12) and which is mounted to be adjustable in an X-ray testing machine (13). The collimation/detector arrangement (13) is adjustable in height relative to the X-ray source (12), and the two are also laterally and synchronously adjustable via respective adjustment elements (5,6). The collimator (13) has a conically-expanding round slot (15), which simulates a predetermined angle ($\Theta_M$) of a scatter-beam path.

6 Claims, 2 Drawing Sheets

OTHER PUBLICATIONS

Bomsdorf, Coherent X–Ray Scatter for Non–Destructive Testing of Works of Art, NDT.net—Dec. 1999, vol. 4, No. 12, pp. 1–10, Proceedings of the 6th Intl. Conf. on "Non–destructive testing and microanalysis for the diagnostics and conservation of the cultural and environmental heritage", Rome, May 17th—20th, p. 941, 1999 (see p. 4 and figure 1).

http://www.heimannsystems.com/newsar.htm, accessed Nov. 6, 2001 (see "Worldwide leadership in X–ray diffraction technology confirmed").

* cited by examiner

APPARATUS FOR DETERMINING THE CRYSTALLINE AND POLYCRYSTALLINE MATERIALS OF AN ITEM

CROSS-REFERENCE TO RELATED APPLICATIONS

This application is a continuation of U.S. application Ser. No. 09/645,486, now abandonded filed Aug. 25, 2000, which is incorporated herein by reference.

FIELD OF THE INVENTION

The invention relates to an apparatus for determining the crystalline and polycrystalline materials of an item.

BACKGROUND OF THE INVENTION

To assure safety in air travel, for example, it is necessary to check luggage (object) with travel items (items), particularly for explosive agents or materials, by employing the most modern technical equipment.

A useful technique for checking for explosives is X-ray diffraction, in which X-rays that are scattered at the crystal structure of an item are measured and compared to the characteristic energy spectra of known explosives. Thus, the spectra of the diffracted rays can indicate the presence of an explosive, and provide information about the explosive material in the object.

An apparatus for executing this method is known from DE 195 10 168 A1. Here, at least one collimator generates a fanned X-ray beam from an X-ray source, which then irradiates a test region of a material to be tested. On the side of the test region opposite the X-ray source, slot-shaped collimators are disposed symmetrically around the axis of the central X-ray beam, in a plane extending perpendicular to the fan plane of the X-ray beam. A plurality of detectors performs an evaluation over the entire X-rayed test region.

EP 0 354 045 A2 also discloses an apparatus and a method in which a fanned X-ray beam is generated. As this fanned X-ray beam radiates through the object to be tested, it is diffracted at the lattice structure of the object. A plurality of detectors records the diffraction as an energy spectrum.

A further apparatus is disclosed in U.S. Pat. No. 4,956, 856. In this case, a narrow X-ray beam (pencil beam) is generated, and directed, by a rotating roller having a spiral-shaped slot, at an object to be X-rayed. The pencil beam passes through the slot transversely to the object to be tested.

DE 41 01 544 A1 discloses the use of a primary beam having a small cross section in an X-ray device. Here, a plurality of detectors and a concentric collimator arrangement detect the scatter radiation generated from the primary beam.

A drawback of the aforementioned apparatuses for checking luggage is that the entire piece of luggage must always be sampled or scanned by X-ray diffraction in order to ascertain all unacceptable luggage items.

An arrangement for generating an expanded X-ray bundle is known from DE 41 30 039 A1. A collimator arrangement used for this purpose comprises two limiting bodies, which are oriented relative to one another such that they limit a space corresponding to the shape of the ray bundle. This arrangement serves to increase the surface impacted by the X-ray.

BRIEF SUMMARY OF THE INVENTION

It is an object of the invention to provide an apparatus of the general type discussed above, for quickly determining the crystalline and polycrystalline materials of an item.

The above object generally is achieved according to the present invention by an apparatus that includes a diffraction apparatus with a collimator/detector arrangement, an X-ray source that is aimed at the collimation/detector arrangement, and a computer. The collimation/detector arrangement is adjustable, both laterally and height-wise relative to the X-ray source, by first adjustment elements. Additionally, the X-ray source is laterally adjustable, by second adjustment elements. Finally, the first and second adjustment elements are synchronously adjustable and are computer controlled by the computer.

The concept underlying the invention is a diffraction apparatus, comprising a collimator/detector arrangement and an X-ray source that is aimed at this arrangement, and which can be brought into and aligned within a testing stage of an X-ray machine through adjustments in height and transverse position. X-ray diffraction is used to determine the material of an item at a predetermined location. To this end, the lateral positions of collimator/detector arrangement and the X-ray source can be adjusted synchronously, with the collimator/detector arrangement also preferably being adjustable in height relative to the X-ray source.

If only two coordinates of a predetermined location (e.g., belt position X and beam to define the lateral position) are known, the adjustable diffraction unit continuously scans the missing third coordinate by moving the collimator/detector arrangement along the measuring path determined by the two coordinates. Consequently, the materials positioned on this line or path can be measured and determined location dependently. If three coordinates of the predetermined location are known, the diffraction apparatus is aimed at this point, and the type of material of the item is determined by, for example, X-ray diffraction analysis, without the need of a measuring sweep.

The height-adjustable collimator/detector arrangement preferably comprises an adjustable round-slot collimator in the form of a truncated cone with a detector disposed behind it.

In a further step of the analysis of the material of an item using the collimator/detector arrangement, additional information on the material can be obtained if, in addition to the diffraction spectrum, the average atomic number of the material is known. For this purpose, the round-slot collimator has a central opening, which is closed to the detector and in which two different, separate detector devices are disposed one behind the other. In a known manner, these detector devices determine the average atomic number of the object located in the primary beam.

The invention is described in detail below with reference to an embodiment illustrated in the drawing.

DETAILED DESCRIPTION OF THE PREFERRED EMBODIMENTS

Figure 1:
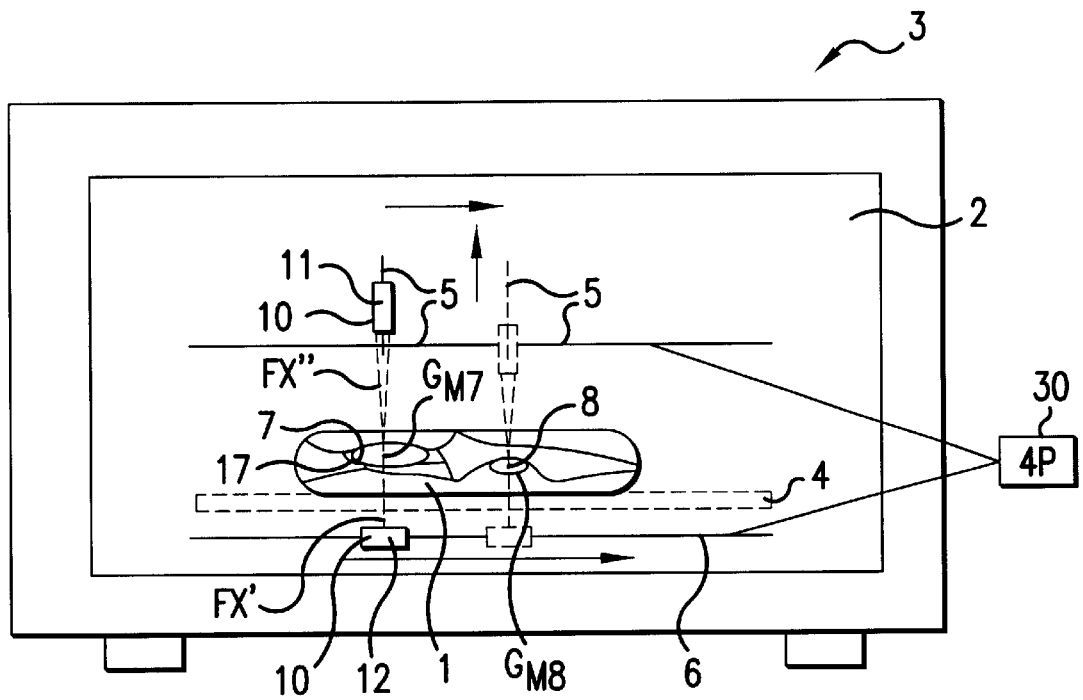
FIG. 1 is a schematic representation of an apparatus according to the invention.

As shown in FIG. 1, an object 1 to be X-rayed is located in an X-ray tunnel 2 of an X-ray testing machine 3. Disposed inside the X-ray tunnel 2 is an adjustable diffraction apparatus 10. The diffraction apparatus 10 comprises a collimator/detector arrangement 11 and an X-ray source 12. The collimator/detector arrangement 11 is aimed at an X-ray beam FX', which is preferably a primary beam emitted as a 'pencil beam' from the X-ray source 12, which is preferably disposed beneath a transport device 4 for the object to be tested in the X-ray tunnel 2. The collimator/detector arrangement (11) is mounted to be adjustable both height-wise and laterally (in the Z and Y directions, respectively, as shown in the figure by arrows) by means of adjustment elements 5, not shown in detail here, connected thereto. The X-ray source 12 is mounted on adjustment elements 6, and can also be adjusted laterally in the Y direction parallel to lateral adjustments of the collimator/detector arrangement (11). The collimation/detector arrangement 11 and the X-ray source 12 are guided synchronously, for which purpose the elements 5 and 6 (which can be, for example, linear guidance with a spindle drive) are actuated at the same time. This movement can be coordinated by a computer 30, not shown in detail. The object 1 to be X-rayed is located, with its items 7, 8, on the transport device 4.

If the primary beam FX' of an X-ray source hits a material, this primary beam FX' is known to be partially deflected at the crystal-lattice structure of the material as scatter radiation FX" (as known from Bragg's Law). Accordingly, the energy spectrum obtained with the energy-sensitive detector yields the crystal structure, and thus the identity of the material. In particular, explosives can be identified and distinguished in this manner.

Figure 2:
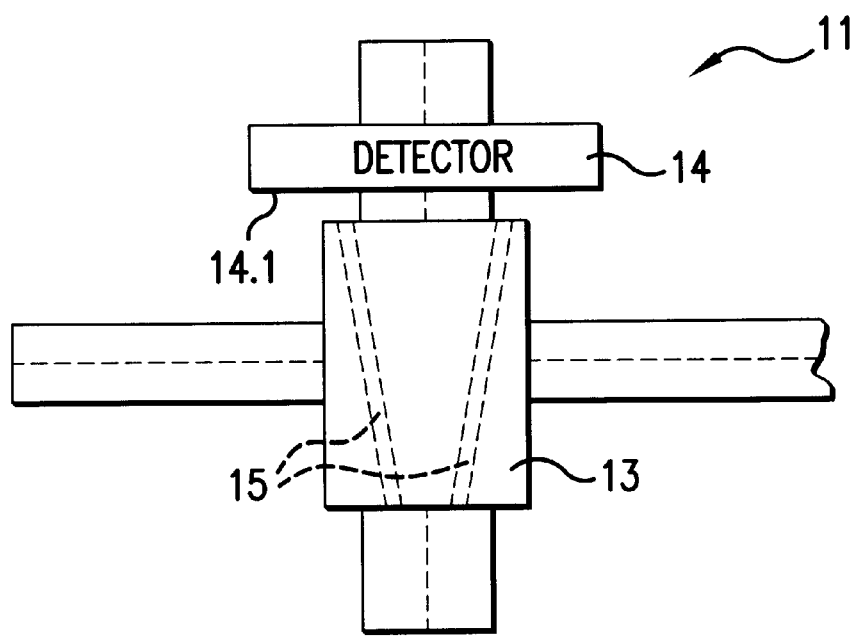
FIG. 2 is a more detailed illustration of the diffraction apparatus of FIG. 1.
Figure 2:
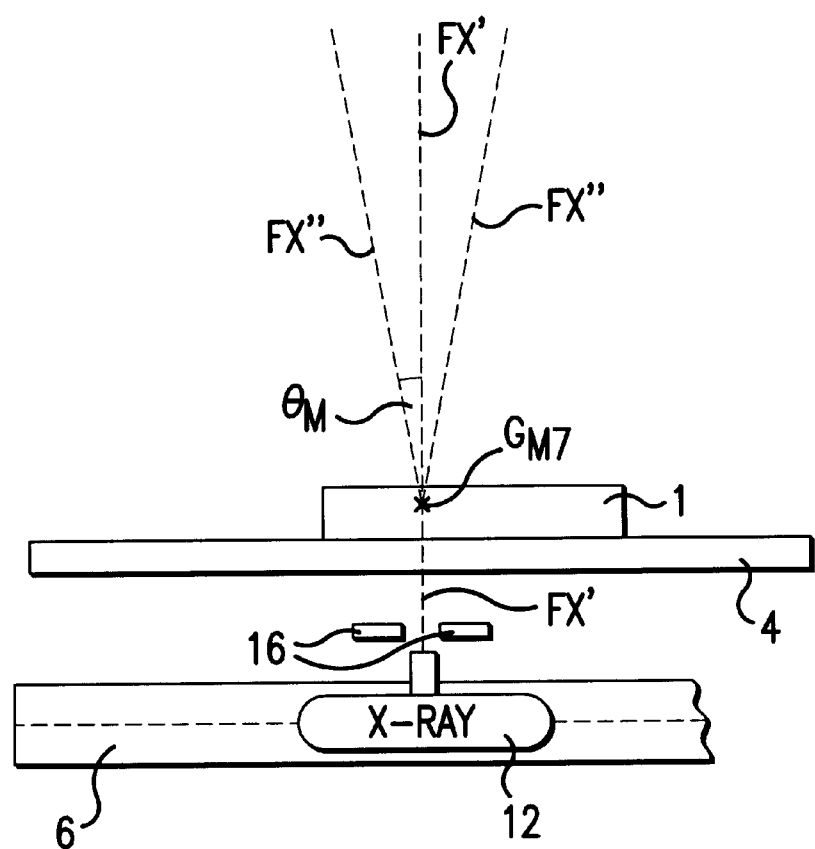

FIG. 2 shows, in detail, the diffraction apparatus 10 according to one embodiment of the present invention for making such X-ray diffraction measurements.

The collimator 13 comprises a round slot 15 which defines a predetermined angle $\Theta_M$ in the form of a truncated cone such that, of the scatter radiation emanating from the tested point $G_{M7}$ of the item 7 in the object, only the components that fall within a specific angle $\Theta_M$ are allowed through to the detector 14. The energy-sensitive detector 14 located behind the collimator 13 detects the scatter radiation FX" passing through round slot 15 at the scatter angle $\Theta_M$. To attain a primary beam FX' from the X-ray source 12, a collimator arrangement 16, for example an apertured-diaphragm arrangement, is mounted in front of the X-ray source 12.

The diffraction apparatus should be aligned to the location of the material to be determined in order to make a X-ray diffraction measurement. If the position information in two spatial coordinates (e.g., transport-device position X and lateral position Y) for the items 7 and 8, for example, is known from a lower or prior test stage, the respective missing coordinate e.g. height must be continuously scanned in a measuring sweep. For this purpose, the transportation device 4 and the collimation/detector arrangement 11 travel to an initial position specified for the respective item 7. From there, the measuring sweep is initiated such that the arrangement 11 travels, as necessary, in its height direction and laterally, synchronously with the X-ray source 12, in the direction of the missing coordinate. The signals recorded by the detector during a measuring sweep are stored in one or more energy spectra and compared in a known manner to known energy spectra in the computer 30. This comparison thus yields the material type, particularly for explosive material.

If the predetermined points $G_{M7}$ and $G_{M8}$ are known in three spatial coordinates, the collimator/detection arrangement 11 and the X-ray source 12 of the diffraction apparatus 10 are displaced and aligned to points $G_{M7}$ and $G_{M8}$ one after the other. The scatter radiation FX" of the X-ray source 12, which is deflected at the crystal lattice of the items 7 or 8, is captured through the round slot 15 of the collimator 13. No further adjustment of the collimator/detection arrangement 11 is necessary during the respective measurement.

It is also possible to combine the coordinate information from the lower test stage and the additional, spatial information from the higher stage, possibly supplemented by numerous measurements along numerous measuring paths, and thus determine the volume and the precise spatial position of, for example, the item 8 in the object 1.

Figure 3A:
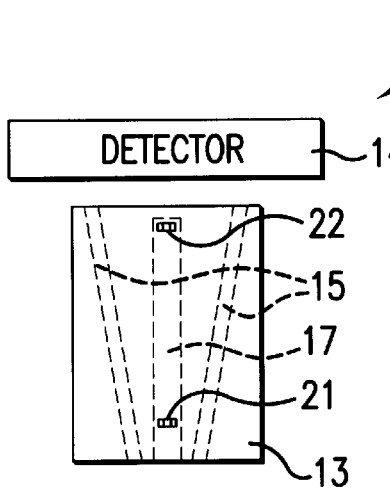
FIGS. 3a and 3b are schematic side and end views of a preferred embodiment of the collimation/detector arrangement of FIG. 2.
Figure 3B:
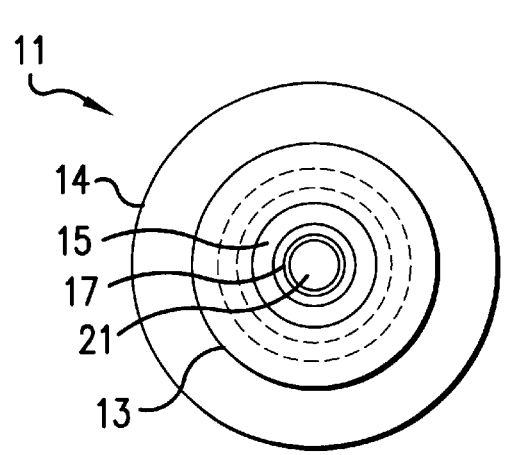

FIG. 3 illustrates an advantageous embodiment of the annular-slot collimator 13. A central, blind-bore-like opening 17 is preferably integrated into the collimator 13. The opening 17 is closed in the direction toward the detector 14 disposed behind it. A first detection device 21 and, disposed behind it at a defined distance, a second detection device 22, are located in the opening 17. The first detection device 21 is embodied as a detector for relatively lower X-ray energies, and the second detection device 22 is embodied as a detector for higher X-ray energies. This collimator 13 can be used, for example, to additionally perform a conventional material detection through the determination of the average atomic number of the material of the item 7 or 8. The combination of this atomic number and the determined energy spectrum can attain an improved identification of the material of the item 7 or 8. This is of particular significance if the item 7 or 8 contains a highly-absorbent material. Often, lower energies of the central beam FX' are absorbed in the material, so the corresponding lines of diffraction are missing in the measured energy spectrum. This absence can be reported to the computer with the additional determination of material, and considered in the comparison for the evaluation.

In addition, the detection devices 21, 22, which can also comprise, for example, quadrant detectors, can perform a precise spatial orientation (alignment) of the collimation/detection arrangement 11 relative to the X-ray source 12. The alignment itself is effected without an object 1 being located between the collimator/detector arrangement 11 and the X-ray source 12. To this end, the collimator 13 described in conjunction with FIG. 2 has the additional opening 17 with the detection devices, which was not shown in detail in FIG. 2 in order to provide a clear overview.

Of course, modifications are possible within the scope of the concept of the invention. For example, other diffraction apparatuses 10 can be used, as are described in the state of the technology, in which case the diffraction apparatus 10, as disclosed in the description, for example, is to be adjustable.

The invention now being fully described, it will be apparent to one of ordinary skill in the art that many changes and modifications can be made thereto without departing from the spirit or scope of the invention as set forth herein.

What is claimed is:

1. An apparatus for determining crystalline and polycrystalline materials of an item in objects, comprising a diffraction apparatus with a collimator/detector arrangement; an X-ray source that emits a primary beam directed towards the collimation/detector arrangement; first adjustment elements for mounting the collimation/detector arrangement for adjustment both laterally and height-wise relative to the X-ray source; second adjustment elements for mounting the X-ray source for lateral adjustment; and a computer for controlling the first and second adjustment elements to move the x-ray source and collimation/detector arrangement in synchronism.

2. The apparatus according to claim 1, wherein the collimation/detector arrangement comprises a detector, and a collimator disposed between a detector and the X-ray source, with the collimator having a conically-expanding round slot, which defines a predetermined angle and with the round slot being oriented toward the detector.

3. The apparatus according to claim 2, wherein the collimator has a central, blind-bore-like opening, which is closed in a direction toward the detector and in which first and second detection devices are located and spaced one behind the other.

4. The apparatus according to claim 3, wherein the first detection device detects relatively lower X-ray energies, and the second detection device detects relatively higher X-ray energies.

5. The apparatus according to claim 2, wherein the collimator/detector arrangement is oriented such that the central bore of the collimator is directed toward the primary beam of the X-ray source.

6. The apparatus of claim 1, wherein the object is luggage, and the x-ray source and collimator/detector arrangement are disposed on opposite sides of a conveyor for the luggage.

* * * * *